United States Patent [19]

Oberg

[11] Patent Number: 5,612,319
[45] Date of Patent: Mar. 18, 1997

[54] POSTEXPOSURE PREVENTION OF HIV INFECTION OR SEROCONVERSION

[75] Inventor: Bo F. Oberg, Upsala, Sweden

[73] Assignee: Medivir AB, Huddinge, Sweden

[21] Appl. No.: 251,316

[22] Filed: May 31, 1994

[51] Int. Cl.$^6$ .................................................. A61K 31/70
[52] U.S. Cl. ......................... 514/49; 514/885; 536/28.2; 536/28.5
[58] Field of Search .................... 536/28.2, 28.5; 514/49, 50, 885

[56] References Cited

U.S. PATENT DOCUMENTS 5,215,970 6/1993 Datema et al. ..................... 514/49

FOREIGN PATENT DOCUMENTS 0391411 10/1990 European Pat. Off. .
WO8808001 10/1988 WIPO .
WO9206102 4/1992 WIPO .

OTHER PUBLICATIONS

Beninger, Paul R. et al., Postexposure Chemoprophylaxis: Approval Criteria for Clinical Trials, Journ. of Acquired Immune Deficiency Syndromes, vol. 4, 1991, (pp. 513–515).
Lange, Joep M.A. et al., Failure of Zidovudine Prophylaxis After Accidental Exposure to HIV–1, New England Jour. Med., May 10, 1990, vol. 322, No. 19 (pp. 1375–1377).
van Rompay, Koen K. et al., Simian Immunodeficiency Virus (SIV) Infection of Infant Rhesus Macaques as a Model to Test Antiretroviral Drug Prophylaxis and Therapy: Oral 3'–Azido–3'–Deoxythymidine Prevents SIV Infection, Antimicrobial Agents and Chemotherapy, Nov. 1992, (pp. 2381–2386).
Fazely, Fatemeh et al., Postexposure Chemoprophylaxis with ZDV or ZDV Combined with Interferon–α: Failure After Inoculating Rhesus Monkeys with a High Dose of SIV, Journ. of Acquired Immune Deficiency Syndromes, 1991, vol. 4, No. 11 (pp. 1093–1097).
Niu, Manette T. et al., Primary Human Immunodeficiency Virus Type 1 Infection: Review of Pathogenesis and Early Treatment Intervention in Humans and Animal Retrovirus Infections, Jour. of Infectious Diseases, 1993, vol. 168, (pp. 1490–1501).
Lundgren, B. et al., Acute Infection of Cynomolgus Monkeys with Simian Immunodeficiency Virus (SIV$_{SM}$) as a Model to Evaluate Antiviral Compounds. Effects of 3'–Azido,3'–Deoxythymidine, Foscarnet and 2',3'–Dideoxycytidine, Antiviral Chemistry & Chemotherapy, 1990, 1(5), (pp. 299–306).
Böttiger, D. et al., Treatment of Acute SIV Infection in Cynomolgus Monkeys with 2',3'–Dideoxyinosine (ddI) and 2',3'–Dideoxythymidiene (d4T), Antiviral Chemistry & Chemotherapy, 1991, 2(6), (pp. 357–361).
Böttiger, D. et al., Prevention of HIV–2 and SIV Infections in Cynomolgus Macaques by Prophylactic Treatment with 3'–Fluorothymidine, Aids Research and Human Retroviruses, vol. 8, No. 7, 1992 (pp. 1235–1238).
Lundgren, Björn et al., Antiviral Effects of 3'–Fluorothymidine and 3'–Azidothymidine in Cynomolgus Monkeys Infected with Simian Immunodeficiency Virus, Journ. of Acquired Immune Deficiency Syndromes, vol. 4, 1991, (pp. 489–498).

*Primary Examiner*—Gary L. Kunz
*Assistant Examiner*—James O. Wilson
*Attorney, Agent, or Firm*—Birch, Stewart, Kolasch & Birch, LLP

[57] ABSTRACT

A method of preventing the establishment of HIV infection and/or HIV seroconversion in a human or simian comprising the administration of an effective amount of the compound 1-[2',3'-dideoxy-3'C-(hydroxymethyl)-β-D-erythropentofuranosyl]-cytosine having the following formula:

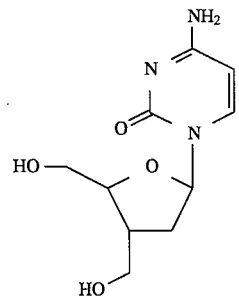

or a pharmaceutically acceptable salt thereof, after exposure of said human or simian to HIV.

24 Claims, No Drawings

POSTEXPOSURE PREVENTION OF HIV INFECTION OR SEROCONVERSION

TECHNICAL FIELD

This invention relates to preventing the establishment of HIV infection and/or HIV seroconversion in a human or simian after exposure to HIV.

Several subpopulations of society, notably health care workers, surgical patients, medical researchers and law enforcement officials are subject to an enhanced risk of coming into accidental contact with human immunodeficiency virus (HIV). For instance, there are dozens of documented seroconversions in health care workers following accidental injury from syringes or surgical instruments previously used by HIV-infected individuals ("needle sticks"). While much can be done to reduce the risk of exposure there remains a need for an effective agent for protecting such individuals and other victims of inadvertant exposure to HIV-positive material from establishing an HIV infection or HIV seroconversion.

DESCRIPTION OF RELATED ART

A small number of antiviral agents, notably AZT (zidovudine) and ddI (dideoxy inosine), have been developed and shown to have a clinically significant action in the suppression of AIDS development or reducing viral loads in HIV-infected individuals. There is some evidence from animal studies that AZT may alter the pattern of lentivirus infections if administered prophylactically. i.e. prior to exposure to HIV or SIV(simian immunodeficiency virus) to delay the onset of viraemia and one report (Van Rompey et al 1992 Antimicrob Agents & Chemotherapy 36 2381–2386) suggests that SIV infection was prevented in 2 infant macacques with AZT given from 2 hours before inoculation, however the low infectious dose renders the significance of the report hard to assess. A further report (Böttiger et al AIDS Res Hum Retroviruses 1992; 7:1235–1238 suggests that FLT (3'-fluorothymidine) administered from 8 hours prior to virus inoculation may provide some protection against SIV. However the majority of literature references point to an inability to prevent infection with SIV with prophylactically, i.e. pre-exposure administered AZT, ddI, ddC, d4T and PFA (Lundgren et al, Antiviral Chemistry & Chemotherapy 1990;5:299–306, Böttiger et al, Antiviral Chemistry & Chemotherapy 1991;6:357–361, Lundgren et al, J AIDS 1991;4:49.8–498) The SIV and HIV-2 infections in monkeys bear a dose resemblance to HIV-I infections in humans.

"Prophylaxis" as used in this technical field generally refers to the administration of an active agent to an at-risk individual in sufficient time to achieve and maintain effective concentrations in the target tissues before the individual enters the risk environment. This is the classic meaning of prophylaxis. The position with regard to postexposure administration of anti-HIV agents is even less satisfactory than the above mentioned prophylactic attempts. There are currently 13 published accounts (Niu et al; J Inf Dis 1993:168:1490–501) of seroconversion after accidental exposure to HIV notwithstanding rapid and sustained postexposure administration of large doses of AZT. Despite many attempts, postexposure treatment has not prevented any HIV-1, HIV-2 or SIV infections (Niu et al, ibid). In other words after extensive research into postexposure infection prevention and FDA consideration of approval criteria (J AIDS 1991;4:513–515), not a single agent has been reported which has proven to prevent the establishment of HIV infection or seroconversion in individuals already exposed to HIV. Not even those experimental agents such as soluble CD4 and heparin sulphate which act in vitro by preventing virus entering target cells and would thus appear to better candidates for prophylaxis than the nucleoside analogues, have proven to have any effect in vivo.

In the therapeutic context (as distinct from prophylaxis), European patent application 0 391 411 A2 describes a family of nucleoside analogues, including the active agent defined below, which family is implicated in the treatment of herpes infections and to some extent exhibits in vitro activity against HIV in a already infected cell line. No teaching or suggestion as to any prophylactic activity is apparent, which is in line with classical expectations as to the efficacy of nucleoside analogues, as discussed above. International patent application nos. WO 88/00050 and WO 92/06102 extend to various nucleoside analogues of this type and demonstrate their activity against established retroviral and HIV infections. However, there is no teaching or suggestion that any of their compounds can be administered after exposure to HIV and yet prevent the establishment of HIV infection or seroconversion.

SUMMARY OF THE INVENTION

The present invention provides a method for preventing the establishment of HIV infection and/or HIV seroconversion in a human or simian comprising the administration of an effective amount of the compound 1-[2',3'-dideoxy-3'-C-(hydroxymethyl)-β-D-erythro-pentofuranosyl]-cytosine having the formula

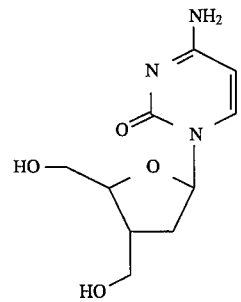

or a pharmaceutically acceptable salt thereof, after exposure of said human or simian to HIV. The invention further provides pharmaceutical compositions for use in this method, comprising an effective amount of the above defined active agent and a pharmaceutically acceptable diluent or carrier therefor.

Alternatively expressed, the invention relates to the use of the above defined active agent in the manufacture of a medicament for postexposure administration to a human or simian to prevent the establishment of HIV infection or seroconversion.

As explained above, not even those prior art antivirals with an established therapeutic activity against HIV-infected cells or with antiviral effects in HIV/AIDS patients can prevent infection when administered after exposure of an individual to HIV, or indeed a monkey to SIV, thus the above defined property of this particular nucleoside anomer is quite unexpected.

The method and composition of the invention should be contrasted with such agents as AZT and ddI which at most appear to delay seroconversion until shortly after "treatment" is concluded and do not prevent the establishment of an HIV infection and ultimately the resulting disease.

The method and compositions of the present invention will be particularly useful for individuals at risk of accidental occupational exposure to HIV-positive material such as the staff or inmates of establishments such as hospitals, prisons and diagnostic or research laboratories. Such establishments can keep supplies of the compositions of the invention for rapid postexposure deployment in the event of accidental exposure to HIV.

The accidental exposure may comprise a needle stick or other surgical injury incurred by health care workers but in a wider context may result from any inadvertant exposure such as through sexual transmission, assault, body fluid splashes, erroneous blood transfusion or reuse of medical implements. An advantage of postexposure administration, as distinct from prophylactic prevention of infection is that it avoids long term administration with potentially expensive agents and improves safety. The currently used HIV agents such as AZT and ddI require life long administration if seroconversion is to be avoided. Additionally, postexposure administration can be extended to individuals not belonging to a high-risk occupation or subpopulation.

Preferably the above defined active agent is administered as soon as practicable following the exposure of the human or simian to HIV. Advantageously administration is commenced within about one day following exposure, especially within eight hours. Preferably administration of the active agent is commenced within about 3 hours following exposure and most preferably within about 1 hour. This timescale allows the above defined active agent to be administered as an oral preparation, such as tablets or syrups or percutaneously as a lotion, suppository or enema. Preferably, however, at least the initial administration following discovery of the accidental exposure is parenteral, eg by subcutaneous, intramuscular or intravenous routes.

Physiologically acceptable salts include, e.g., salts of organic carboxylic acids such as acetic, lactic, gluconic, citric, tartaric, maleic, malic, panthothenic, isethionic, oxalic, lactobionic and succinic acids; organic sulfonic acids such as methanesulfonic, ethanesulfonic, benzenesulfonic, p-chlorobenzenesulfonic and p-toluenesulfonic acids and inorganic acids such as hydrochloric, hydroiodic, sulfuric, phosphoric and sulfamic acids.

While it is possible for the active agent to be administered alone, it is preferable to present it as part of a pharmaceutical formulation. Such a formulation will comprise the above defined active agent together with one or more acceptable carriers and optionally other therapeutic ingredients. The carrier(s) must be acceptable in the sense of being compatible with the other ingredients of the formulation and not deleterious to the recipient.

The formulations include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product.

Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in off liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate and other metallic stearates, stearic acid, silicone fluid, talc waxes, oils and colloidal silica. Flavouring agents such as peppermint, oil of wintergreen, cherry flavouring or the like can also used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Formulations suitable for topical administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Formulations suitable for topical administration to the skin may be presented as ointments, creams, gels, and pastes comprising the active agent and a pharmaceutically active carrier. An exemplary topical delivery system is a transdermal patch containing the active agent.

Formulations for rectal or vaginal administration may be presented as a suppository or pessary with a suitable base comprising, for example, cocoa butter or a salicylate. Other vaginal preparations can be presented as tampons, creams, gels, pastes, foams or spray formulations containing, in addition to the active agent, such carriers as are known in the art to be appropriate.

Formulations suitable for nasal administration wherein the carrier is a solid include a coarse powder having a particle size, for example, in the range 20 to 500 microns which is administered in the manner in which snuff is taken, i.e. by rapid inhalation from a container of the powder held up dose to the nose. Suitable formulations wherein the carrier is a liquid for administration, for example, as a nasal spray or as nasal drops, include aqueous or oily solutions of the active agent.

Formulations suitable for parenteral administration include aqueous and nonaqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in freeze-dried (lyophilized) condition requiting only the addition of the sterile liquid carrier, for example water for injection, immediately prior to use. Extemporaneous injection solutions and suspensions may be prepared from sterile powders, granules, and tablets of the kind previously described.

In view of the understandable shock attendant upon either the exposure to HIV, i.e. a needle stick, or its discovery, e.g. that a contaminated syringe has been been reused, the above defined active agent is advantageously presented in an easily administered, rapidly acting form. An example of such a dosage form or package is a self-administered spring-loaded syringe currently used for nerve gas antidotes.

Several administration routes may be administered simultaneously, for instance a vaginal preparation, an intramuscular injection and a tablet may be contemporaneously taken, e.g. in the event of a suspected sexual transmission, to provide effective doses immediately at the site of exposure and in the circulatory system and for a more sustained rate via the oral route.

The above defined active agent is administered following exposure to HIV in an amount effective to prevent HIV infection or HIV seroconversion. Suitable amounts include about 0.1 mg/kg bodyweight/day, preferably at least about 0.5 mg/kg/day and more preferably about 10 mg/kg/day. This corresponds to a preferred dosage amount of about 10 mg to about 10 g per day. Larger dosage regimes will tend to be indicated where a particularly large inoculum is suspected to have been transmitted, such as through a contaminated blood line or transfusion, where sustained administration is impractical, such as in a military environment, where the active agent is administered as a single dose "morning after pill" by clinics lacking follow up facilities or where there has been extended delay before the active agent is first administered.

The maximum dosage of the active agent is of course dependent on toxicity and the bioavailability of the dosage route employed but it is noted that unlike therapeutic treatment for established HIV infections with the currently available agents which must be administered indefinitely in order to suppress viraemia, the present invention contemplates administration during a finite period following exposure to HIV. Accordingly transient toxicity which would be intolerable to a long term therapeutic regime may be tolerated in the method of the present invention. Cell culture results indicate that the above defined compound is generally well tolerated by human cells, for instance the $ID_{50}$ in MT4 cells appears to be around 45 µg/ml. In vivo simian experiments indicate no detectable toxicity short term at 30 mg/kg/day and bearing in mind the finite administration period, dosages of 100 mg/kg/day or more are feasible.

Accordingly, in view of the two immediately preceding paragraphs, preferred dosage amounts include a range of from 0.1 to 100 mg/kg bodyweight/day, particularly 0.5 mg/kg/day to 50 mg/kg/day and more particularly 1.0 to 25 mg/kg/day.

The finite period of time mentioned in the penultimate paragraph above will be the period of time which is sufficient to prevent the establishment of HIV infection or HIV seroconversion when administered after exposure to HIV, but is not so long as to incur unnecessary expense or risk cumulative toxicity in atypically sensitive individuals. The finite period of administration will preferably be at least about one day, preferably about 3 days and may be 1 or two weeks, especially where there has been significant delay between exposure to HIV and initial administration of the active agent. Sustained release dosage forms can of course be formulated to release the active agent for the period intended, either as a single dose, or as a twice daily, daily or weekly dosage unit.

In keeping with sound pharmaceutical practice in relation to antiviral agents, the compositions of the invention may comprise one or more auxilliary antivirals or antimicrobials as congeners etc, either against other common infective agents in HIV positive body fluids or samples, such as hepatitis B or C, or those in use in conventional double or multiple therapy against HIV. Examples of such auxilliaries include interferon, gamma-globulin, RT and protease inhibitors, AZT and ddI. The compositions of the invention may alternatively or additionally comprise an abortificient such as the oestrogen derivatives employed in "morning after pills" or RU 486.

DETAILED DESCRIPTION

Embodiments of the invention will now be described by way of example only with reference to the following Examples.

EXAMPLE 1

Preparation of 1-[2',3'-dideoxy-3'C-(hydroxymethyl)-β-D-erythro-pentofuranosyl]-cytosine The benzoyl protected sugar residue, methyl-5-O-benzoyl-3-[(benzoyloxy)methyl]-2,3-dideoxy-D-erythro-pentafuranoside is prepared according to the method of Svensson et al; 1991, 56, 2993–2997. The base residue is prepared by suspending 120 mg, 1.08 mmol cytosine in 0.2 ml trimethylchlorosilane and 2 ml hexamethyldisilazane along with crystalline ammonium, sulphate, refluxing until clear, vacuum concentration and coevaporation with dry xylene. This preparation is dissolved in 2 ml dichloroethane in a nitrogen atmosphere before 170 mg, 0.46 mmol of the sugar residue is added followed by 0.22 ml, 0.96 mmol t-butyldimethyltriflate, Reaction proceeds for 24 hours at room temperature and is quenched with saturated sodium hydrogen carbonate during agitation for half an hour. This solution is diluted with dichloroethane, washed in the saturated carbonate and concentrated following drying and filtration. The resultant concentrate is subjected for 24 hours at room temperature to 20 ml of saturated methanolic ammonia before being concentrated, dissolved in water and extracted with dichloroethane. A C18 column is used for reverse phase semi preparative chromatography on the concentrated aqueous phase and eluted with 2% methanol in water. The β anomer, 1-[2',3'-dideoxy-3'C-(hydroxymethyl)-β-D-erythro-pentofuranosyl]-cytosine follows the α anomer and collected fractions yielded 27 mg with the following NMR spectra in ppm (using TMS and TSP or dioxane as internal standards) $[a]^{26}_D$: +64° (c 0.27, $H_2O$); UV ($H_2O$) λmax: 272 nm (ε9208); $^1$H-NMR (270 MHz, $D_2O$): 2.2–2.46 (m, 3H, H-2); H-3'); 3.68 (d, $J_{3',6}$=5.5 Hz, 2H, H-6'); 3.76 (dd, $J_{4',5'a}$=12.5 Hz, 1H, H-5'a); 3.92 (dd, $J_{4',5'b}$=2.9 Hz, $J_{5'a,5'b}$=12.5 Hz, 1H, H-5'b); 4.01 (m, $J_{3',4}$=8.1 Hz, $J_{5'a, 4}$=5.5 Hz, $J_{5'b,4}$=2.9 Hz, 1H, H-4'); 6.05 (3, $J_{5,6}$=7.3 Hz, 1H, H-5); 6.11 (dd, $J_{1',2'a}$=7.0 Hz, $J_{1',2'b}$=4.0 Hz, 1H, H-1'); 7.91 (d, $J_{5,6}$=7.3 Hz, 1H, H-6); $^{13}$C-NMR (25.05 MHz, $D_2$): 36.1 (c-2'); 40.8 (C-3') 62.7, 63.1 (C-5', C-6'); 84.7, 87.1 (C-1', C-4'); 96.5 (C-5); 142.2 (C-6); 158.2 (C-2); 166.8 (C-4).

The chromatographically pure compound is prepared into a subcutaneous preparation by dissolving 3.00 g in 300 ml 0.9% NaCl in pyrogen free water followed by sterile filtration to give a 10 mg/ml solution which is administered subcutaneously at the rate of 1 mg/kg bodyweight.

EXAMPLE 2

Animal Experiments

Inoculation: The control and test animals, 2 year old macaque monkeys were inoculated subcutaneously with either a moderate (10 monkey infectious doses $MID_{50}$, as determined by Böttiger et al Antiviral Chemistry and Chemotherapy 1992;3:269–271) or a high (100 $MID_{50}$) dose preparation of SIV in phosphate buffer, as listed in Table 1 below.

One or three hours after i.v. inoculation with SIV, paired test animals were injected subcutaneously with 10 mg/kg of the preparation of Example 1, repeated three times per day for 1 day or 3 days as listed in table 1. Blood samples were extracted from the test and control animals on days 0, 17, 23 and 30 for determination of SIV antibody, SIV p26 antigen and presence of infective virus. The methods have been described by Böttiger et al, AIDS Res Hum Retroviruses 1992;7:1235–1238.

With reference to table 1, it is dear that the administration of the present active agent prevented the infection establishing itself in the test animals, as monitored by the presence of viral antigen or antibody to the virus in the blood or ability to culture virus. All of the control animals exhibited positive SIV antibody and antigen titres within the first 23 days and within 30 days infectious SIV virus could be cultivated. In contrast, a single day of treatment at this dosage rate protected the test animals from 10 infectious doses of SIV. During the 30 day period monitored each of the test animals was free from detectable SIV antibody or SIV antigen and infectious virus could not be cultivated from blood samples at day 30. It should be noted that an inoculum of 10 infectious doses is a significantly greater amount of virus than is exposed in most accidental exposures of the needle stick variety. As can be seen from animal nos 53 and 58 slightly longer treatment duration of 3 days protected the test animals from the very high dose of 100 infectious doses of SIV inoculated into each animal.

TABLE 1

| Monkey No. | Infective dose HIV-2 $MID_{50}$ | Treatment start post inoculation hours | Treatment duration days | Detected during 30 days post virus inoculation | | |
|---|---|---|---|---|---|---|
| | | | | SIV A6 | SIV Ag | SIV-2 |
| 41 | 10 | – | – | + | + | + |
| 42 | 10 | – | – | + | + | + |
| 43 | 10 | – | – | + | + | + |
| 44 | 10 | – | – | + | + | + |
| 45 | 10 | 1 | 1 | – | – | – |
| 46 | 10 | 1 | 1 | – | – | – |
| 48 | 10 | 1 | 3 | – | – | – |
| 49 | 10 | 1 | 3 | – | – | – |
| 54 | 10 | 3 | 3 | – | – | – |
| 57 | 10 | 3 | 3 | – | – | – |
| 53 | 100 | 1 | 3 | – | – | – |
| 58 | 100 | 1 | 3 | – | – | – |

EXAMPLE 3

Injectable preparation 750 mg of lyophilized active agent, as prepared in Example 1, is dissolved in 100 ml of pyrogen free isotonic saline. The pH of the preparation is adjusted to 7.5 with 0.1M NaOH/HCl and the preparation sterile filtered and aseptically decanted into 10 10 ml sterile vials having a rubber diaphragm in the lid for rapid withdrawal of the contents. Each vial represents a dosage form containing 75 mg of active ingredient suitable for providing a dosage of 1 mg/kg for a normal adult male.

EXAMPLE 4

Capsules 12 g of active agent, as prepared in Example 1, is seived through US 60 mesh along with 12 g of dessicated lactose and 0.1 g of magnesium stearate. The resultant fine powder is dosed in 500 mg amounts into hard gelatin capsules to form dosage units of 245 mg representing a dosage of about 32 mg/kg for a normal adult male.

EXAMPLE 5

Sustained release preparation

The following materials are wet granulated in a 300 mg povidone aqueous base:

5000 mg active agent 1000 mg HPMC (Methocel K4M premium)

500 mg lactose (pharmaceutical grade)

The granules are compressed with a trace of magnesium stearate into 700 mg tablets suitable for twice daily administration.

I claim:

1. A method of inhibiting the establishment of HIV infection in a human or simian following exposure to a potential infection establishing amount of HIV, comprising administering to said human or simian an effective anti-HIV establishment amount of the compound:

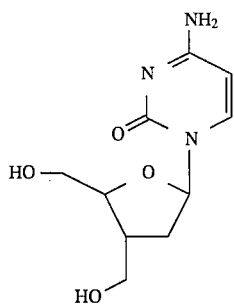

1. 1-[2',3'-dideoxy-3'-C-(hydroxymethyl)-β-D-erythro-pentofuranosyl]cytosine or a pharmaceutically acceptable salt thereof.

2. A method according to claim 1, wherein said administering commences within about 8 hours after said human or simian has been exposed to HIV.

3. A method according to claim 2, wherein said administering commences within about 3 hours after said human or simian has been exposed to HIV.

4. A method according to claim 3, wherein said administering commences within about 1 hour after said human or simian has been exposed to HIV.

5. A method according to claim 1 wherein said administration is continued over at least 1 day.

6. A method according to claim 5 wherein said administration is continued over at least 3 days.

7. A method according to claim 5 wherein said administration is continued for less than two weeks.

8. A method according to claim 1 wherein said effective amount comprises at least 0.1 mg/kg body weight/day.

9. A method according to claim 8 wherein said effective amount comprises at least 10 mg/kg body weight/day.

10. A method according to claim 1 wherein at least the initial administration of said compound is intravenous, subcutaneous or intramuscular.

11. A method according to claim 1, wherein said administering commences within about 1 day after said human or simian has been exposed to HIV.

12. A method according to claim 1, wherein said administering occurs for 3 days.

13. A method of inhibiting HIV seroconversion in a human or simian following exposure to a potential seroconversion amount of HIV, comprising administering to said human or simian an effective anti-HIV seroconverting amount of the compound:

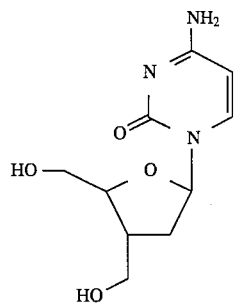

1-[2',3'-dideoxy-3'C-(hydroxymethyl)-β-D-erythro-pentofuranosyl]cytosine or a pharmaceutically acceptable salt thereof.

14. A method according to claim 13 wherein said administering commences within about 8 hours after said human or simian has been exposed to HIV.

15. A method according to claim 14 wherein said administering commences within about 3 hours after said human or simian has been exposed to HIV.

16. A method according to claim 15 wherein said administering commences within about 1 hour after said human or simian has been exposed to HIV.

17. A method according to claim 13 wherein said administering is continued over at least one day.

18. A method according to claim 17 wherein said administering is continued over at least three days.

19. A method according to claim 17 wherein said administering is continued for at least two weeks.

20. A method according to claim 13 wherein said effective amount comprises at least 0.1 mg/kg body weight/day.

21. A method according to claim 20 wherein said effective amount comprises at least 10 mg/kg body weight/day.

22. A method according to claim 13 wherein at least the initial administering of said compound is intravenous, subcutaneous or intramuscular.

23. A method according to claim 13 wherein said administering commences within about 1 day after said human or simian has been exposed to HIV.

24. A method according to claim 13, wherein said administering occurs for 3 days.

* * * * *